United States Patent

Berghall

(10) Patent No.: US 9,463,456 B2
(45) Date of Patent: Oct. 11, 2016

(54) ELECTRONIC PIPETTE

(71) Applicant: Thermo Fisher Scientific Oy, Vantaa (FI)

(72) Inventor: Suvi Berghall, Espoo (FI)

(73) Assignee: Thermo Fisher Scientific Oy, Vantaa (FI)

( * ) Notice: Subject to any disclaimer, the term of this patent is extended or adjusted under 35 U.S.C. 154(b) by 0 days.

(21) Appl. No.: 14/275,956

(22) Filed: May 13, 2014

(65) Prior Publication Data

US 2014/0334993 A1 Nov. 13, 2014

(30) Foreign Application Priority Data

May 13, 2013 (FI) ...................................... 20135494

(51) Int. Cl.
*B01L 3/02* (2006.01)

(52) U.S. Cl.
CPC ........ *B01L 3/0237* (2013.01); *B01L 2200/087* (2013.01); *B01L 2300/027* (2013.01); *B01L 2400/0478* (2013.01)

(58) Field of Classification Search
CPC .................................................... B01L 3/0237
USPC ........................................................ 422/501
See application file for complete search history.

(56) References Cited

U.S. PATENT DOCUMENTS

| 5,689,286 | A | 11/1997 | Wugofski |
| 2007/0276546 | A1 | 11/2007 | Molitor |
| 2008/0011042 | A1 | 1/2008 | Molitor et al. |
| 2008/0210023 | A1* | 9/2008 | Telimaa et al. ............ 73/864.18 |
| 2009/0074622 | A1 | 3/2009 | Kalamakis et al. |
| 2012/0291567 | A1 | 11/2012 | Homberg et al. |

FOREIGN PATENT DOCUMENTS

| EP | 2 224 324 A1 | 9/2010 | |
| WO | 2005/079989 A1 | 9/2005 | |
| WO | WO 2012045418 A1 * | 4/2012 | ............ B01L 3/0227 |

OTHER PUBLICATIONS

National Board of Patents and Registration of Finland, Search Report, Patent Application No. 20135494, mailed Jan. 17, 2014 (2 pages).

* cited by examiner

*Primary Examiner* — Paul Hyun
(74) *Attorney, Agent, or Firm* — Wood, Herron & Evans, LLP

(57) ABSTRACT

An electronic pipette comprising a piston actuated in a cylinder by a motor, a control system for carrying out pipette operations, and a user interface for operating the pipette, which user interface comprises a display, wherein the main menu of the user interface comprises a user defined shortcut to a specific pipetting application.

5 Claims, 3 Drawing Sheets

ELECTRONIC PIPETTE

CROSS-REFERENCE TO RELATED APPLICATIONS

The present application claims priority under 35 U.S.C. §119 of Finnish Patent Application No. 20135494, filed May 13, 2013, the disclosure of which is hereby incorporated herein by reference in its entirety.

FIELD OF THE INVENTION

The present invention relates to an electronic pipette intended for use in the dosage of liquids and comprising a piston actuated in a cylinder by a motor, a control system for carrying out pipette operations, and a user interface for operating the pipette, which user interface comprises a display.

BACKGROUND OF THE INVENTION

Electronic pipettes comprising a user interface with a display for displaying information and data are known from prior art. Generally, these known user interfaces also include buttons, switches or other kind of means for making selections, inputting data, browsing menus and/or activating selected pipetting operations with the help of the display.

Publication WO 2005/079989 discloses an electronic pipette comprising a control system and a user interface with a display and inputting/selection means, where the control system comprises at least two pipetting setting arrays, each setting array comprising at least one setting that acts over the entire volume range and that can be changed separately for each array of settings, whereby a desired setting array can be selected for use in each case. The setting arrays can be saved and named as separate profiles, for example, for different users. The setting arrays and profiles can also be equipped with a locking function, with a password protection, for example, which prevents unauthorized use and/or changes to the settings.

One known type of user interface is known from U.S. Publication No. 2009/0074622 A1, which user interface is menu-driven and allows the user to program pipetting operations and/or applications having a plurality of pipetting actions or steps.

The use of electronic pipettes is increasing, but even though their advantages, such as time savings, decrease in repetitions, etc., most of the pipettes presently sold are still manual pipettes. One reason for this is the higher price of the electronic pipettes, but ease of use of the manual pipettes has also significant effect.

Even though the user interfaces of the electronic pipettes have developed greatly in recent years, they are still quite inflexible and not very well adaptable to user needs. Therefore, most of the users still use manual pipettes or use only portion of the actions and possibilities provided by the electronic pipettes.

Electronic pipettes are also generally used by different users and in different applications. Due to the complex user interface, many users do not save the settings but change them manually when required. This continuous editing of the settings increases the possibility of editing and programming errors, which increases the risk of pipetting errors, especially if the user does not notice that the application or action has been modified by other user or even by him-/herself.

SUMMARY OF THE INVENTION

In order to overcome at least partially the above-mentioned problems and to improve the user interface and usability of an electronic pipette, the present invention provides an electronic pipette where the main menu of the user interface comprises a user defined shortcut to a specific pipetting application.

With this kind of shortcut to a specific pipetting application located in the main menu of the user interface, the user can quickly and easily proceed to carry out the specific pipetting application without the need to go through plurality of sub menus and different settings.

Advantageously, the shortcut in the main menu of the user interface in the present invention is displayed as a user definable and modifiable icon, whereby it is easy to present the shortcut in the main menu easily identifiable to the user, with a specific form and coloring of the icon, for example. This is especially helpful where there is, for example, a plurality of user defined shortcuts in the main menu.

In the present invention, the specific pipetting application comprises advantageously a plurality of pipetting actions. These pipetting actions may be in a suitable sequence, for example. The pipetting actions may include, for example, ejecting the tip of the pipette, filling of the tip container, dispensing the tip container, as well as pipetting functions comprising plurality of actions, such as direct pipetting, reverse pipetting, repetitive reverse pipetting, stepped pipetting, diluting, and mixing, for example.

The specific pipetting application may advantageously be user definable, via the user interface of the pipette, for example.

The specific pipetting application, and the relating shortcut as well as the relating icon, may also advantageously be preprogrammed, with a computer, for example, and input into the user interface. This type of preprogramming is much easier and quicker than setting the shortcut and the specific pipetting application up through the user interface of the electronic pipette. The preprogrammed specific pipetting applications can also easily be distributed to different electronic pipettes.

In the present invention, the specific pipetting applications may advantageously be password protected, so that other users cannot change the settings or actions of the pipetting application, or so that only authorized persons may modify the settings and actions of the specific pipetting application.

In the present invention, the main menu of the user interface of the electronic pipette may be completely user definable and modifiable. This way the main menu can, for example, consist only of shortcut icons to different predefined specific pipetting actions.

The electronic pipette of the present invention is advantageously a handheld entity, which may have a separate charging station, which charging station may also advantageously be used for inputting preprogrammed shortcuts, specific pipetting actions and other data into the control system and/or user interface of the electronic pipette.

BRIEF DESCRIPTION OF THE DRAWINGS

Exemplifying embodiments of the present invention and its advantages are explained in greater detail below in the sense of an example and with reference to the accompanying drawings, where.

DETAILED DESCRIPTION OF THE INVENTION

Figure 1:
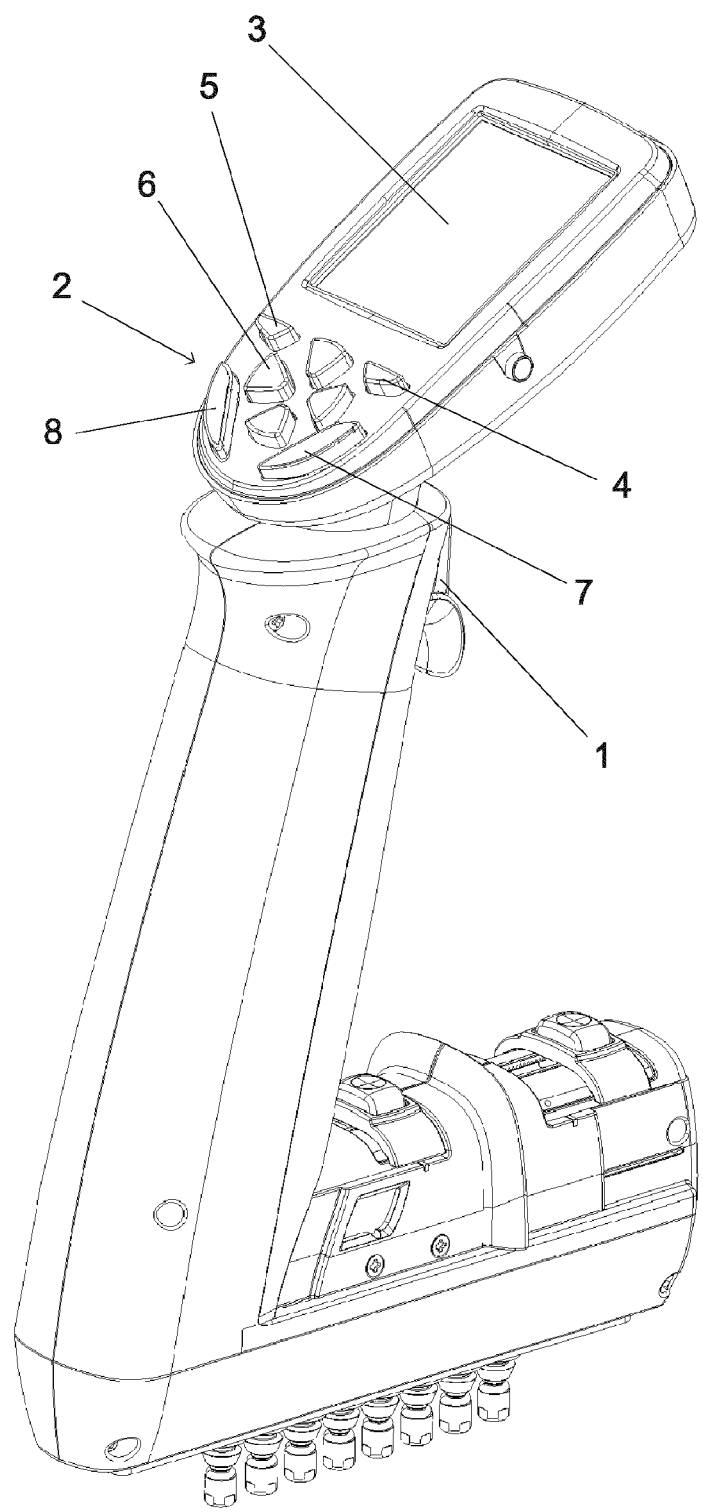
FIG. 1 shows schematically an electronic pipette according to one embodiment of the present invention.

FIG. 1 shows schematically an electronic pipette according to one embodiment of the present invention, which is driven with an electric motor. The user interface of the control system comprises an operating switch 1, a keyboard 2 and a display 3. The pipette shown in FIG. 1 is a handheld entity, which in this embodiment is an electronic multichannel pipette.

The display 3 is disposed at the top of the pipette, in a position upwardly oblique away from the keyboard 2 on the upper surface of a projection. A power source is provided within the projection. The keyboard 2 is disposed on the upper surface of the projection at its end on the side of the body. The display shows necessary information relating to the use of the pipette, such as, e.g., the pipette volume and function in use and the current function step. The display also shows depending on the situation different menus, in which different actions, settings and applications may be selected or modified.

Navigation and selections on the menu presented in the display is carried out by means of the keyboard 2. The keyboard keys are: a right-hand selection key 4, a left-hand selection key 5, arrow keys 6, right-hand tip removal key 7 and left-hand tip removal key 8. The current is switched on by depressing any key. Depending on the menu displayed, the selection keys allow the user to move forwards or backwards in the menu hierarchy or to start using a selected function or application. Depending on the menu displayed, the arrow keys allow the user to move to an option on the display or to change characters on the display (such as digits or writing). The selection function enables the user to move to the desired location in the menu and to confirm it by means of the selection keys. The characters may act on a setting of the function (e.g., volume, piston stroke speed), selecting function or application, or they may give some information.

Figure 2:
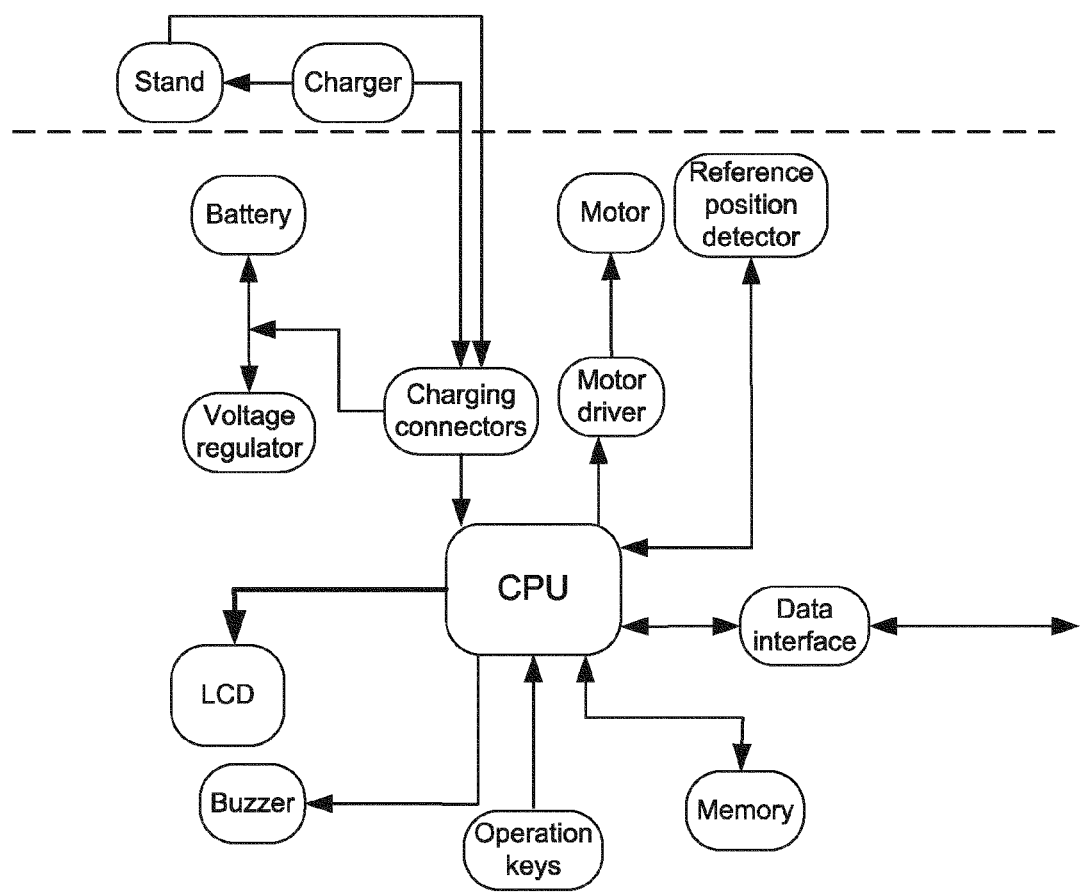
FIG. 2 shows schematically a functional diagram of an electronic pipette according to one embodiment of the present invention.

FIG. 2 shows a functional diagram of an electronic pipette. The core of the control system is a central processing unit (CPU) connected with a memory. The CPU is used by means of the operation keys, i.e., the operating switch 1 and the keyboard 2. The CPU is informed of the piston position by a reference position sensor. The CPU gives the commands needed for actuating the piston to a motor driver, which controls a motor. The functions are indicated on the display (liquid crystal display LCD). Some functions are indicated with acoustic signals by means of a buzzer. In addition, the CPU is connected to a data interface allowing data input into or output from the CPU. A chargeable battery acts as the voltage source. The battery comprises a voltage regulator. In this embodiment the battery is charged through charging connectors using a charger in a stand. The charging is also controlled by the CPU.

In FIG. 2, the parts under a dash line are included in the handheld entity of the electronic pipette, whereas the parts above the dash line form a separate stand.

FIGS. 3A-3I show an example of steps for creating a shortcut in a main menu of a user interface of an electronic pipette according to one embodiment of the present invention.

Figure 3A:
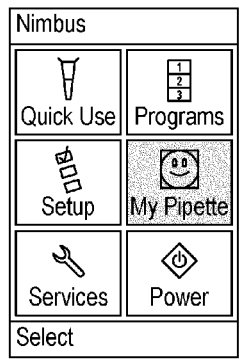
FIGS. 3A-3I show an example of steps for creating a shortcut in a main menu of a user interface of an electronic pipette according to one embodiment of the present invention.

FIG. 3A shows a main menu of a user interface of an electronic pipette according to one embodiment of the present invention. This menu includes as a default key functions and settings relating the use of the electronic pipette. The main menu also includes option named as "My pipette" which allows the user to define and modify personal shortcuts for specific pipetting actions, and to personalize the main menu of the pipette.

Figure 3D:
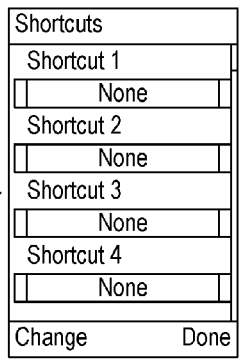
Figure 3G:
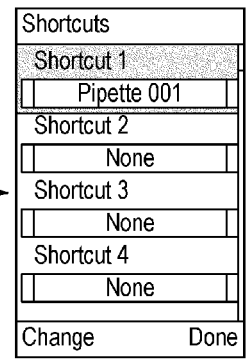
Figure 3B:
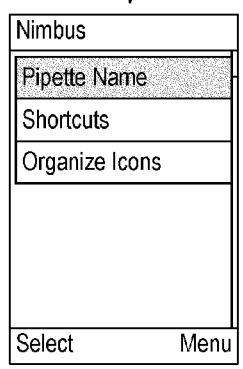

When the option "My pipette" is selected from the main menu, a "My pipette" menu is opened in the display of the pipette showing options "Pipette Name", "Shortcuts" and "Organize Icons", as shown in FIG. 3B. The option "Pipette Name" allows the user to give a specific name to the pipette, the option "Shortcuts" allows the user to create specific pipetting applications and relating shortcuts to these applications and modify these, and the option "Organize Icons" allows the user to add, modify and remove icons on the main menu.

Figure 3E:
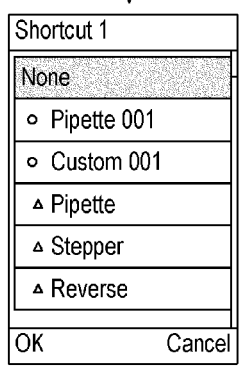
Figure 3H:
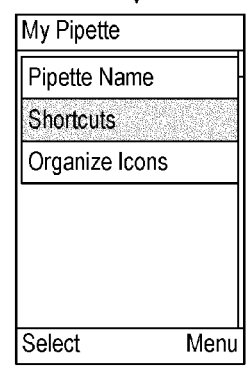
Figure 3C:
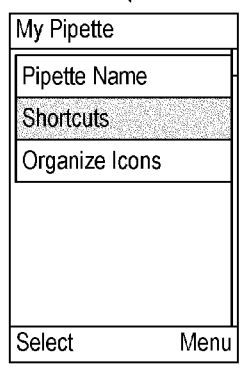

When the option "Shortcuts" is selected from the "My pipette" menu, as shown in FIG. 3C, a "Shortcuts" menu is opened with four numbered shortcut options, as shown in FIG. 3D. In the situation of FIG. 3D, there are no defined shortcuts, since all of the numbered shortcuts are defined as "None".

For proceeding to define a shortcut, option "Shortcut " is selected from "Shortcuts" menu, which selection opens a "Shortcut 1" menu, as shown in FIG. 3E. The "Shortcut 1" menu displays plurality of options for pipetting actions and pipetting applications, as well as possible preset or preprogrammed pipetting applications.

Figure 3F:
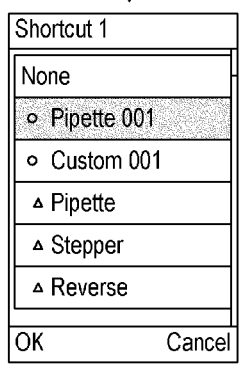

From the "Shortcut 1" menu is selected option "Pipette 001" which is, for example, a preprogrammed pipetting application, as shown in FIG. 3F. After this selection is accepted, the previous "Shortcuts" menu is opened, where the "Shortcuts 1" option now shows the set "Pipette 001" application, as shown in FIG. 3G. When the wanted changes to this "Shortcuts" menu are done, the use returns to the "My pipette" menu, as shown in FIG. 3H.

Figure 3I:
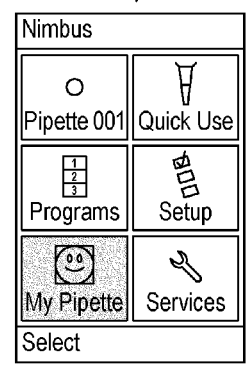

When the user returns from the "My pipette" menu to the main menu, a new shortcut "Pipette 001" is created in the main menu, as is shown in FIG. 3I.

The user may change the location of this new shortcut "Pipette 001" by returning to the "My pipette" menu shown in FIGS. 3B and 3H, and selecting the "Organize Icons" option, which allows the user to move and delete existing icons in the main menu.

Now, when the option "Pipette 001" is selected from the main menu, the electronic pipette proceeds directly to carry out the defined actions defined in this application with the defined settings.

The icon for the shortcut can be defined to be uniform for all shortcuts, the icon can be included in the pipetting application option, or the icon can be created and/or modified by the user with the user interface of the pipette, for example.

While the present invention has been illustrated by description of various embodiments and while those embodiments have been described in considerable detail, it is not the intention of Applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of Applicant's invention.

What is claimed is:

1. An electronic pipette, comprising:
   a body, said body housing:
   a piston actuated in a cylinder by a motor,
   a control system for carrying out pipette operations, and
   a user interface for operating the pipette, which user interface comprises a display, wherein a main menu on the display of the user interface is modifiable by a user, via the user interface of the pipette, to comprise at least two user defined shortcuts to specific user defined pipetting applications.

2. An electronic pipette according to claim 1, wherein at least one of the at least two shortcuts is displayed as a user definable and modifiable icon.

3. An electronic pipette according to claim 1, wherein at least one of the specific pipetting applications comprises a plurality of pipetting actions.

4. An electronic pipette according to claim 1, wherein at least one of the specific pipetting applications and/or settings of the at least one specific pipetting application are password protected.

5. An electronic pipette according to claim 1, wherein the main menu of the user interface is completely user definable and modifiable.

* * * * *